US008043449B1

(12) United States Patent
Przybelinski et al.

(10) Patent No.: US 8,043,449 B1
(45) Date of Patent: Oct. 25, 2011

(54) APPARATUS AND METHOD FOR FABRICATING SHEAR TEST COUPONS

(75) Inventors: Emily Przybelinski, Everett, WA (US); Aaron Coon, Marysville, WA (US); Gary David Benham, Marysville, WA (US); Michael J. Badgley, Bothell, WA (US)

(73) Assignee: The Boeing Company, Chicago, IL (US)

( * ) Notice: Subject to any disclaimer, the term of this patent is extended or adjusted under 35 U.S.C. 154(b) by 101 days.

(21) Appl. No.: 12/479,776

(22) Filed: Jun. 6, 2009

(51) Int. Cl.
*B32B 38/00* (2006.01)

(52) U.S. Cl. .......... 156/64; 156/350; 156/378; 156/379; 73/150 A; 73/826; 73/827; 73/841; 73/842; 73/845

(58) Field of Classification Search ............... 73/150 A, 73/826, 827, 841, 842, 845; 156/60, 64, 156/288, 295, 304.1, 304.5, 350, 378, 379, 156/580
See application file for complete search history.

(56) References Cited

U.S. PATENT DOCUMENTS

| | | |
|---|---|---|
| 4,957,004 A | 9/1990 | McKinlay et al. |
| 5,142,905 A * | 9/1992 | Ezzo et al. .................. 73/150 A |
| 5,176,028 A | 1/1993 | Humphrey |
| 5,753,823 A | 5/1998 | Chang et al. |
| 2008/0245843 A1 * | 10/2008 | Suga et al. .................. 228/3.1 |

FOREIGN PATENT DOCUMENTS

WO    WO 2005071735 A1 *   8/2005

* cited by examiner

*Primary Examiner* — Matthew Daniels
*Assistant Examiner* — Joshel Rivera
(74) *Attorney, Agent, or Firm* — Klintworth & Rozenblat IP LLC (57) ABSTRACT

An apparatus for adhering coupons together for adhesive shear testing may include a first member, a second member, at least one alignment device, and at least one separation device. The first member may have at least one first member cavity for holding at least one first member coupon. The second member may have at least one second member cavity for holding an overlapping area of at least one second member coupon adjacent to and separate from the at least one first member coupon. The overlapping area of the at least one second member coupon may be adhered to the at least one first member coupon. The at least one alignment device may control a size of the overlapping area. The at least one separation device may control a separation distance between the overlapping area of the at least one second member coupon and the at least one first member coupon.

26 Claims, 12 Drawing Sheets

APPARATUS AND METHOD FOR FABRICATING SHEAR TEST COUPONS

FIELD OF THE INVENTION

The disclosure relates to apparatus and methods for adhering coupons together for adhesive shear testing.

BACKGROUND OF THE DISCLOSURE

Apparatus and methods exist for adhering coupons together for subsequent adhesive shear testing. Many of the existing apparatus and methods may have one or more of the following issues: the use of inaccurate weight systems being used to adhere the coupons; un-precise coupon overlap measuring systems; the inability to allow adhesive to squeeze out from the coupons during bonding; difficulty removing the adhered coupons from the fabrication apparatus; difficulty in controlling bond thickness of the adhesive used to adhere the coupons; the use of tooling having excessive parts increasing cost; the requirement of a cutting process to cut the coupons which may weaken the coupon bond-line; and/or one or more other types of issues. Each of these issues may lead to inaccurate adhesive shear testing results.

An apparatus and/or method is needed which may solve one or more problems of one or more of the conventional apparatus and methods for adhering coupons together for adhesive shear testing.

SUMMARY OF THE DISCLOSURE

In one embodiment, an apparatus is provided for adhering coupons together for adhesive shear testing. The apparatus may include a first member, a second member, one or more alignment devices, and one or more separation devices. The first member may include one or more first member cavities for holding one or more first member coupons. The second member may include one or more second member cavities for holding an overlapping area of one or more second member coupons adjacent to and separate from the one or more first member coupons. In such matter, the overlapping area of the one or more second member coupons may be adhered to the one or more first member coupons. The one or more alignment devices may control a size of the overlapping area. The one or more separation devices may control a separation distance between the overlapping area of the one or more second member coupons and the one or more first member coupons.

In another embodiment, a method is provided for adhering coupons together for adhesive shear testing. In one step, a second member may be aligned relative to a first member using one or more separation devices. In such manner, one or more surfaces of the second member may be located at a distance apart from one or more surfaces of the first member. In another step, first member coupons may be located into first member cavities of the first member. In yet another step, second member coupons may be located into second member cavities of the second member against one or more adjustable alignment devices. Overlap areas of the second member coupons may be controllably overlapped relative to the first member coupons. Adhesive may be located between the overlap areas of the second member coupons and the first member coupons. In an additional step, pressure may be applied to adhere the second member coupons to the first member coupons using the adhesive.

These and other features, aspects and advantages of the disclosure will become better understood with reference to the following drawings, description and claims.

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims.

Figure 1:
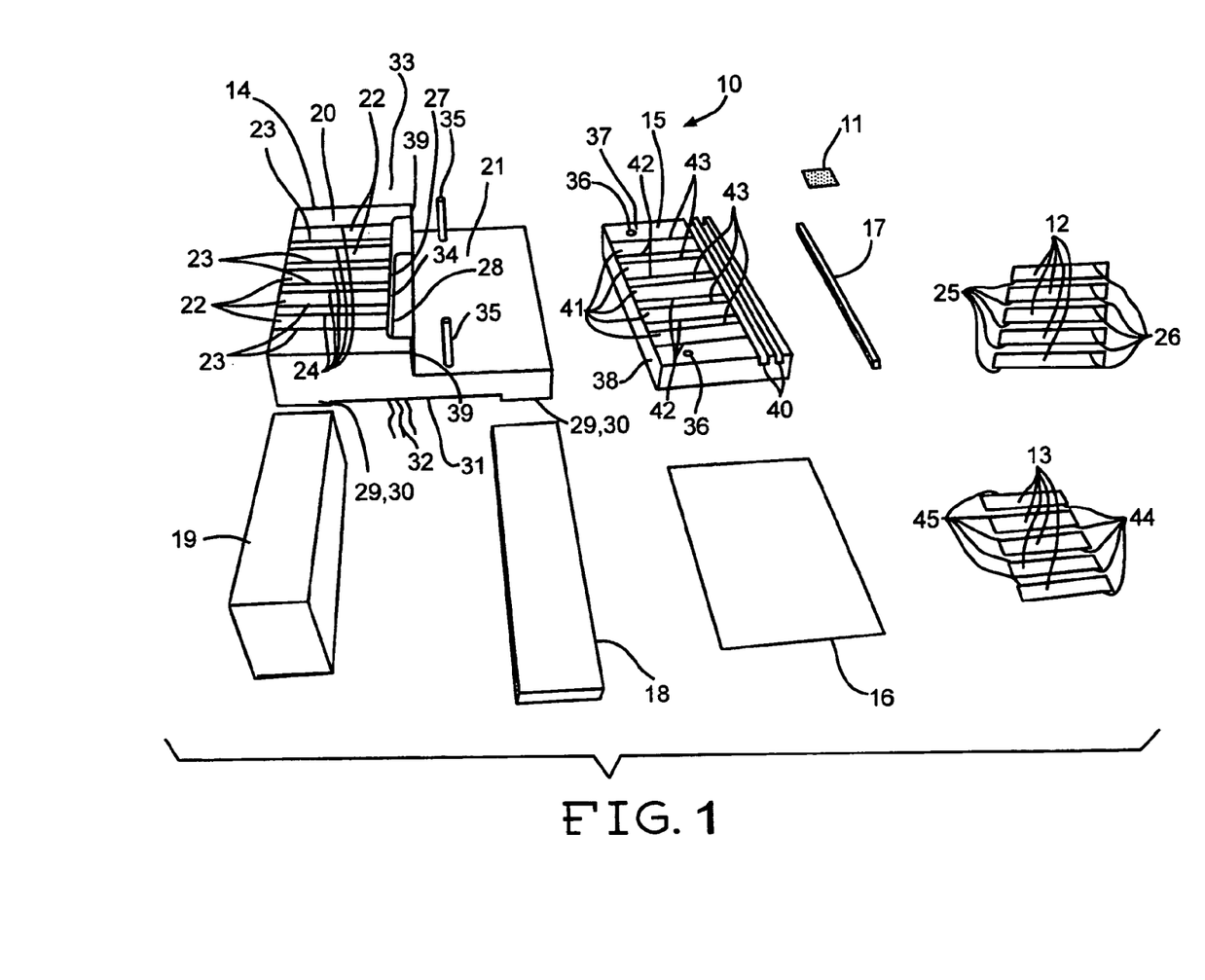
FIG. 1 illustrates a top perspective view of one embodiment of a disassembled apparatus for adhering, using adhesive, at least one first member coupon to at least one second member coupon.

FIG. 1 illustrates a top perspective view of one embodiment of a disassembled apparatus 10 for adhering, using adhesive 11, at least one first member coupon 12 to at least one second member coupon 13. The adhered coupons 12 and 13 may subsequently be shear tested to test the strength of the adhesive 11 holding the coupons 12 and 13 together. The apparatus 10 may comprise a first member 14, a second member 15, at least one separation device 16, at least one alignment device 17, a press-member 18, and a weight 19.

The first member 14 may comprise a base, and the second member 15 may comprise a separate top member for being disposed on top of the first member 14. The first member 14 may comprise stepped flat support surfaces 20 and 21 disposed at differing heights. Flat support surface 20 may comprise at least one first member cavity 22. The at least one first member cavity 22 may comprise a plurality of adjacent first member cavities 22 each having side-walls 23 and 24 spaced apart to abut against respective side surfaces 25 and 26 of separate first member coupons 12 placed in the respective first member cavities 22. In such manner, separate first member coupons 12 may be secured in place in separate respective first member cavities 22 in the flat support surface 20.

A chamfered groove 27 may be disposed between the stepped flat support surfaces 20 and 21. The chamfered groove 27 may extend from a lower surface 28 of the first member 14 through the flat support surface 20. A plurality of leg surfaces 29 may be disposed on a bottom 30 of the first member 14. A slot 31 may extend between the leg surfaces 29 to allow air 32 to freely flow between the chamfered groove 27 and the slot 31 to escape to the ambient atmosphere 33. A groove wall-surface 34 may extend from the lower surface 28 of the first member 14 to the flat support surface 20. The groove wall-surface 34 may be perpendicular to the stepped flat surfaces 20 and 21. At least one pin 35 may be attached to and extend perpendicularly from the flat support surface 20 and parallel to the groove wall-surface 34. The at least one pin 35 may be adapted to secure the second member 15 to the first member 14 by extending through at least one hole 36 in the second member 15. The first member 14 may be made of a non-stick plastic such as Polyoxymethylene, commonly known under DuPont's brand name Delrin. Polyoxymethylene may comprise the chemical formula $-(-O-CH_2-)_n-$. In other embodiments, the first member 14 may be made of another type of non-stick material to avoid the first member coupons 12 from sticking within the respective first member cavities 22.

The at least one separation device 16 may comprise at least one shim. The at least one separation device 16 may be adapted to be disposed on the flat support surface 21 of the first member 14. The second member 15 may be adapted to be disposed on the at least one separation device 16 which may be disposed on the flat support surface 21 of the first member 14. By using one or more separation devices 16 of varying heights, a flat support surface 37 of the second member 15 may be disposed at varying distances above the flat support surface 20 of the first member 14.

The second member 15 may be substantially rectangular. When the second member 15 is disposed on the at least one separation device 16 on top of the flat support surface 21 of the first member 14, with the pins 35 extended through the holes 36 in the second member 15, a side surface 38 of the second member 15 may abut against side surfaces 39 of the first member 14. In such manner, the second member 15 may be secured in place relative to the first member 14. The at least one alignment device 17 may comprise at least one of a stopper and a surface of the second member 15. The second member 15 may comprise at least one slot 40. The at least one alignment device 17 may be adapted to be disposed within the at least one slot 40 to extend past the flat support surface 37 of the second member 15. The second member 15 may comprise a plurality of slots 40 located in varying positions in the flat support surface 37 of the second member 15. By moving the at least one alignment device 17 into varying located different slots 40, the position of the at least alignment device 17 relative to the flat support surface 37 of the second member 15 may be altered.

Flat support surface 37 may comprise at least one second member cavity 41. The at least one second member cavity 41 may comprise a plurality of adjacent second member cavities 41 each having side-walls 42 and 43 spaced apart to abut against respective side surfaces 44 and 45 of separate second member coupons 13 placed in the respective second member cavities 41. Separate second member coupons 13 may be secured in place in separate respective second member cavities 41 in the flat support surface 37 with ends 46 of the second member coupons 13 abutting against the at least one alignment device 17 located within one of the slots 40. In such manner, by aligning the second member coupons 13 within the second member cavities 41 of the second member 15 against the alignment device 17 which has been located in a particular positioned slot 40, the second member coupons 13 may overlap the first member coupons 12 by a predetermined amount. The second member 15 may be made of a non-stick plastic such as Polyoxymethylene, commonly known under DuPont's brand name Delrin. Polyoxymethylene may comprise the chemical formula $-(-O-CH_2-)_n-$. In other embodiments, the second member 15 may be made of another type of non-stick material to avoid the second member coupons 13 from sticking within the respective second member cavities 41. By varying the height of the at least one separation device 16, the second member coupons 13 may be disposed a predetermined separation distance above the first member coupons 12.

The press-member 18 may be adapted to be disposed on and over an overlapping area of the first and second member coupons 12 and 13. The weight 19 may be adapted to be disposed on and over the press-member 18 in order to press the second member coupons 13 towards the first member coupons 12 in order to compress adhesive 11 between the first and second member coupons 12 and 13. In such manner, the first and second member coupons 12 and 13 may be adhered together.

Figure 2:
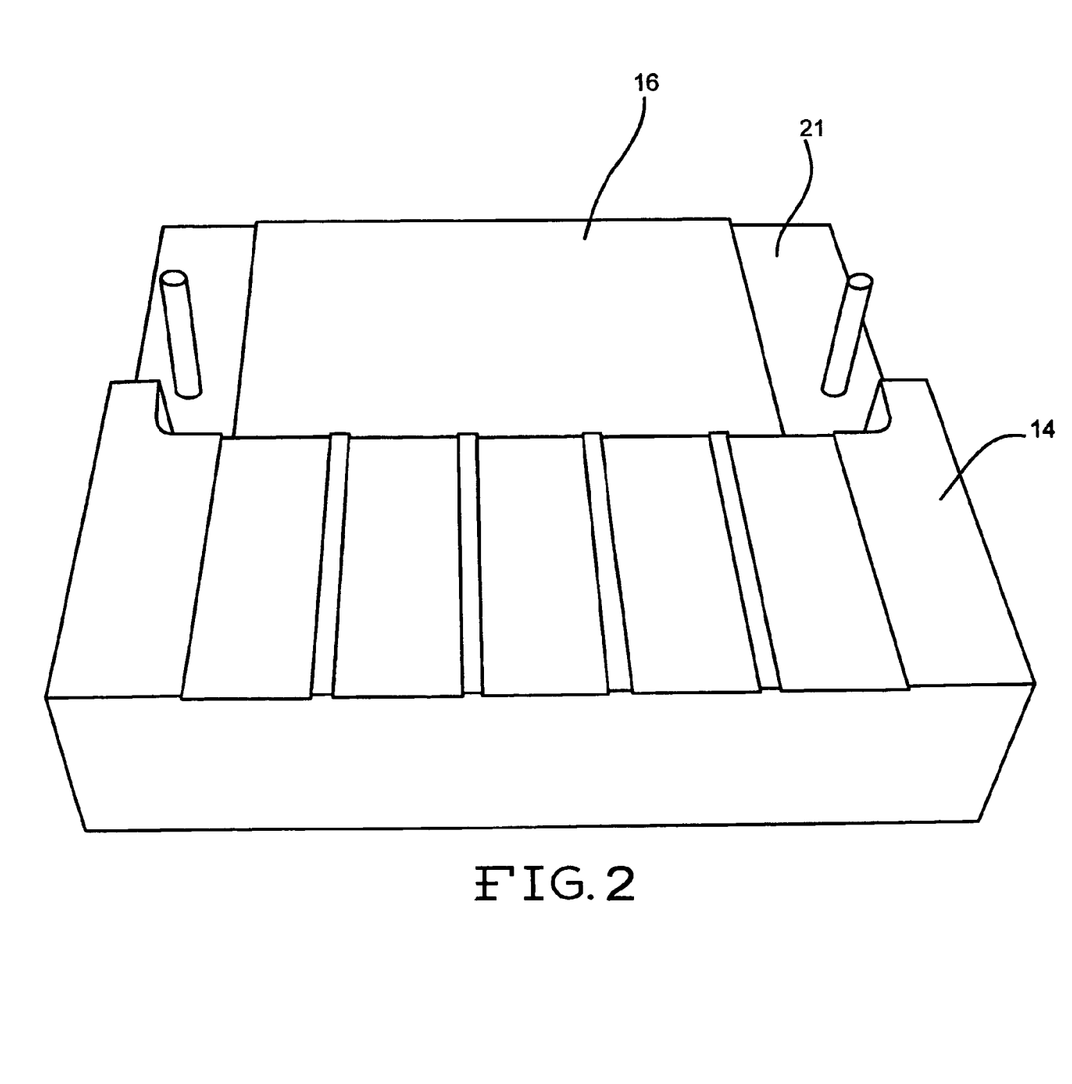
FIG. 2 illustrates a top perspective view of a first member of the apparatus of FIG. 1 with at least one separation device having been placed on a flat support surface of the first member.

FIG. 2 illustrates a top perspective view of the first member 14 of FIG. 1 with the at least one separation device 16 having been placed on the flat support surface 21 of the first member 14.

Figure 3:
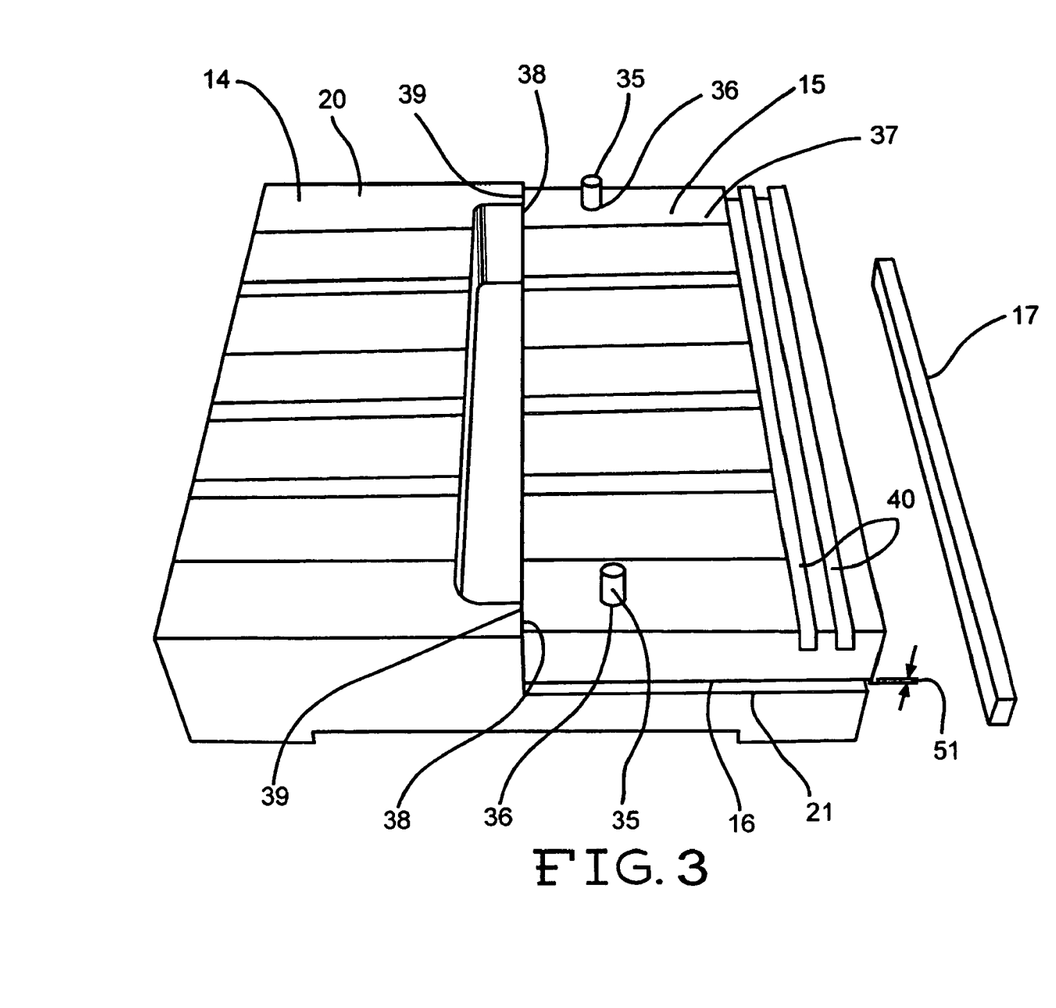
FIG. 3 illustrates a top perspective view of the first member of FIG. 2 with pins of the first member extended through holes of a second member to locate the second member on the at least one separation device on the flat support surface of the first member.

FIG. 3 illustrates a top perspective view of the first member 14 of FIG. 2 with the pins 35 of the first member 14 having been extended through the holes 36 of the second member 15 to locate the second member 15 on the at least one separation device 16 disposed on the flat support surface 21 of the first member 14. Side surface 38 of the second member 15 may be abutted against side surfaces 39 of the first member 14 to further hold the second member 15 in place. As a result of the height 51 of the separation device 16, the flat support surface 37 of the second member 15 may be disposed apart from and above at least one of the flat support surface 20 of the first member 14 and the first member coupons 12 (shown in FIG. 5).

Figure 4:
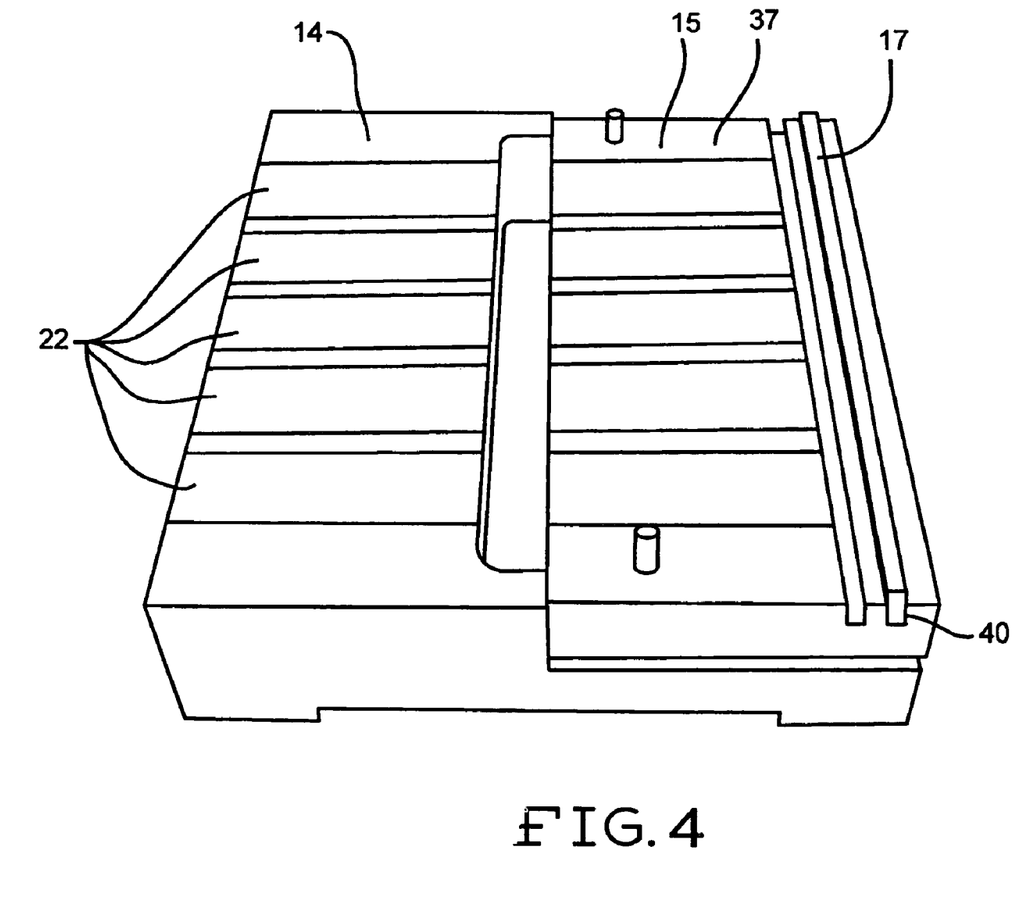
FIG. 4 illustrates a top perspective view of the first and second members of FIG. 3 with at least one alignment device having been placed into a slot in a flat support surface of the second member.

FIG. 4 illustrates a top perspective view of the first and second members 14 and 15 of FIG. 3 with the at least one alignment device 17 having been placed into one of the slots 40 in the flat support surface 37 of the second member 15.

Figure 5:
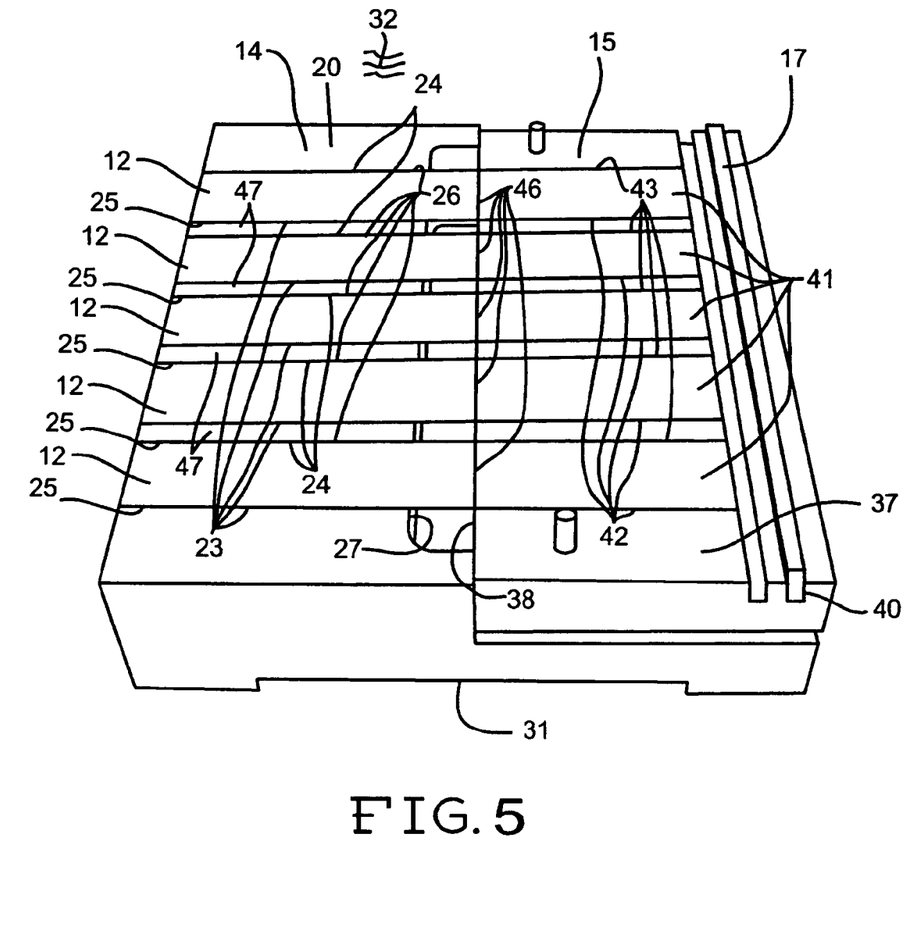
FIG. 5 illustrates a top perspective view of the first and second members of FIG. 4 with the first member coupons having been placed into first member cavities of the flat support surface of the first member.

FIG. 5 illustrates a top perspective view of the first and second members 14 and 15 of FIG. 4 with the first member coupons 12 having been placed into the first member cavities 22 of the flat support surface 20 of the first member 14. The side surfaces 25 and 26 of each first member coupon 12 may be abutted against the side-walls 23 and 24 of each respective first member cavity 22 (shown in FIG. 4). Ends 46 of the first member coupons 12 may be abutted against side surface 38 of the second member 15 to further hold the first member coupons 12 in place in the desired alignment. The first member cavities 22 may be spaced apart to provide gaps 47 between the first member coupons 12. The gaps 47 between the first member coupons 12 may allow air 32 to flow out of and into the chamfered groove 27 between the first and second members 14 and 15 and out of and from the slot 31 of the first member 14.

Figure 6:
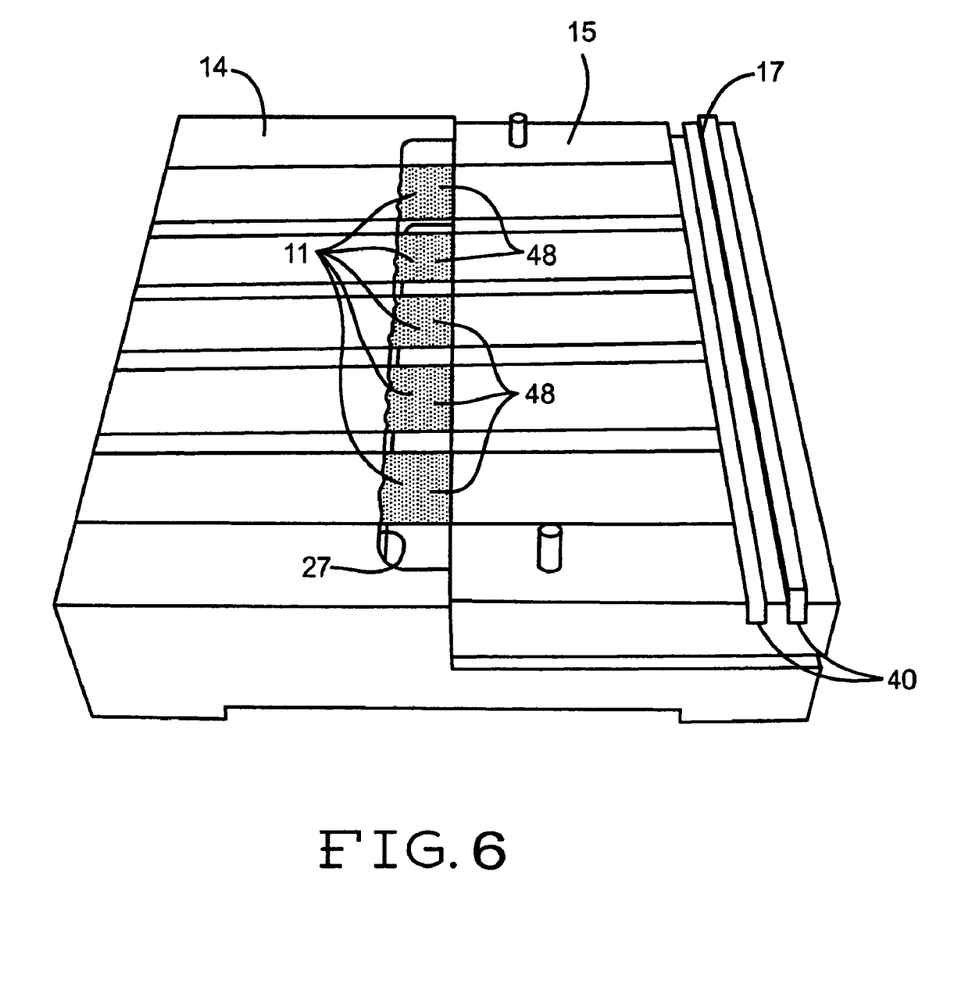
FIG. 6 illustrates a top perspective view of the first and second members of FIG. 5 with adhesive having been placed in a bond area of the first member coupons.

FIG. 6 illustrates a top perspective view of the first and second members 14 and 15 of FIG. 5 with adhesive 11 having been placed in a bond area 48 of the first member coupons 12. Some or all of the bond area 48 may be disposed over the chamfered groove 27.

Figure 7:
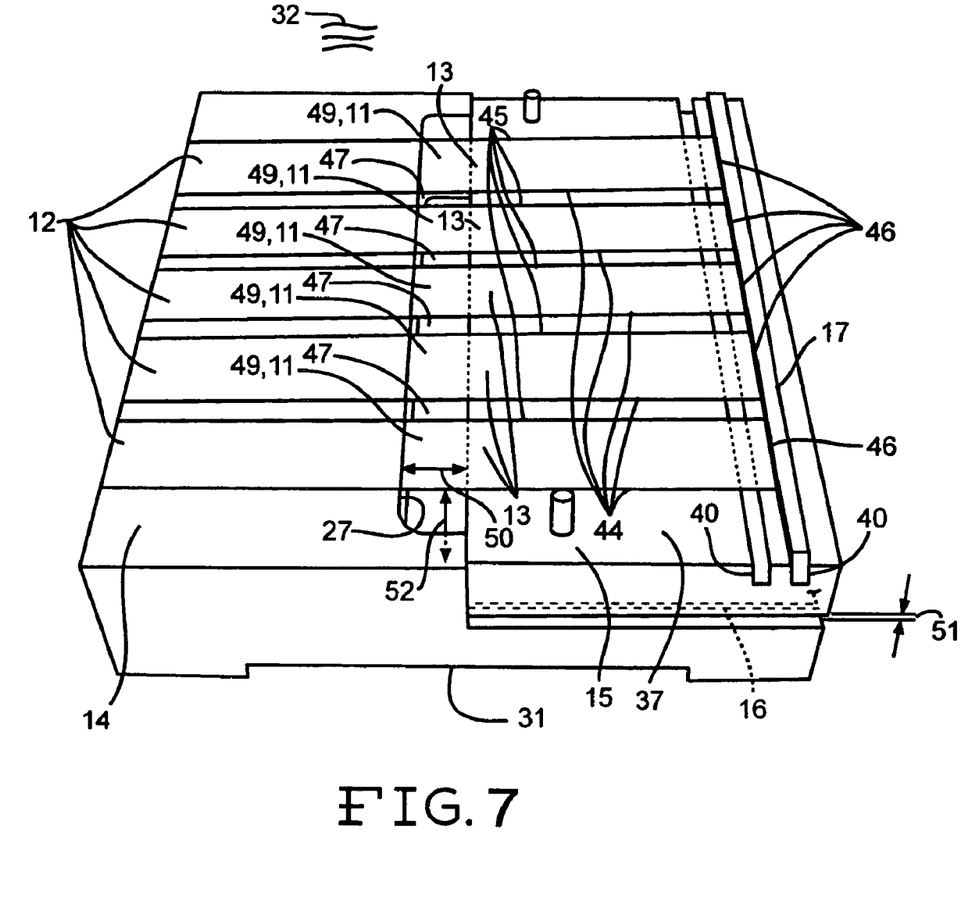
FIG. 7 illustrates a top perspective view of the first and second members of FIG. 6 with second member coupons having been placed into second member cavities of the flat support surface of the second member to overlap the first member coupons.

FIG. 7 illustrates a top perspective view of the first and second members 14 and 15 of FIG. 6 with the second member coupons 13 having been placed into the second member cavities 41 (as shown by FIG. 5) of the flat support surface 37 of the second member 15. The side surfaces 44 and 45 of each second member coupon 13 may be abutted against the side-walls 42 and 43 (as shown by FIG. 5) of each respective second member cavity 41 (as shown by FIG. 5). Ends 46 of the second member coupons 13 may be abutted against the at least one alignment device 17 located within the slot 40 in order to precisely align the second member coupons 13 to have overlapping areas 49 which overlap the first member coupons 12 by a desired amount. The at least one alignment device 17 may control a size of the overlapping areas 49. The overlapping areas 49 of the second member coupons 13 may be disposed adjacent to and separate from the first member coupons 12.

As a result of the height 51 of the at least one separation device 16, the second member coupons 13 may be vertically aligned a separation distance 52 apart from and above the first member coupons 12 in the overlapping areas 49. The adhesive 11 may be disposed in the overlapping areas 49 extending between the first and second member coupons 12 and 13. The second member cavities 41 (as shown in FIG. 5) may be substantially horizontally aligned with the first member cavities 22 (as shown in FIG. 4) in order to preserve the gaps 47 between the first member coupons 12 over the chamfered groove 27. In such manner, air 32 may flow out of and into the chamfered groove 27 between the first and second members 14 and 15 and out of and from the slot 31 of the first member 14. This may allow the air 32 to circulate around the overlapping areas 49.

By locating the at least one alignment device 17 in varying located slots 40 in the flat surface 37 of the second member 15, the size and/or length 50 of the overlapping areas 49 of the second member coupons 13, which overlap the first member coupons 12, may be precisely controlled. Further, by varying a height 51 of the at least one separation device 16, the separation distance 52 between the first and second member coupons 12 and 13 in the overlapping areas 49 may be precisely controlled. As a result, by varying the location of the at least one alignment device 17 and by varying the height 51 of the at least one separation device 16, the size (including respectively length and height) of the adhesive 11 in the overlapping areas 49 may be precisely controlled.

Figure 8:
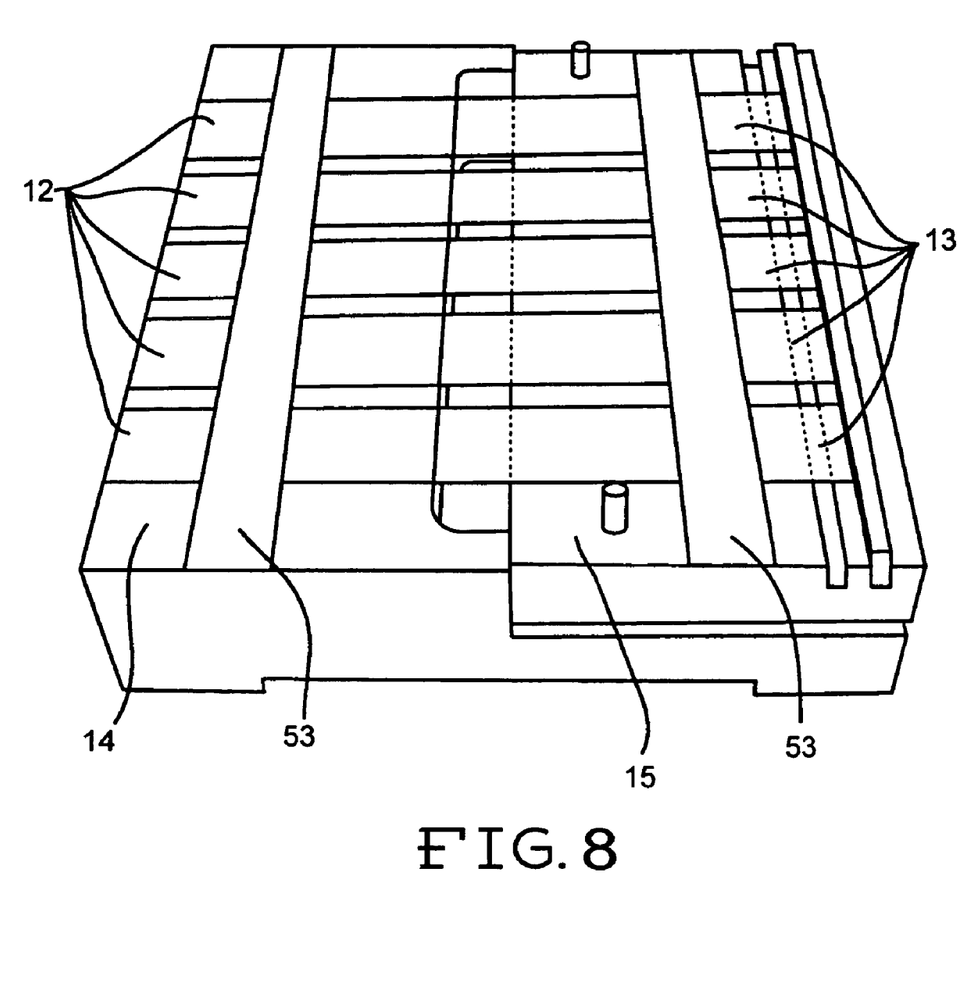
FIG. 8 illustrates a top perspective view of the first and second members of FIG. 7 with tape having been placed over the first and second member coupons to hold the first and second member coupons in position relative to the first and second members.

FIG. 8 illustrates a top perspective view of the first and second members 14 and 15 of FIG. 7 with tape 53 having been placed over the first and second member coupons 12 and 13 to hold the first and second member coupons 12 and 13 in position relative to the first and second members 14 and 15.

Figure 9:
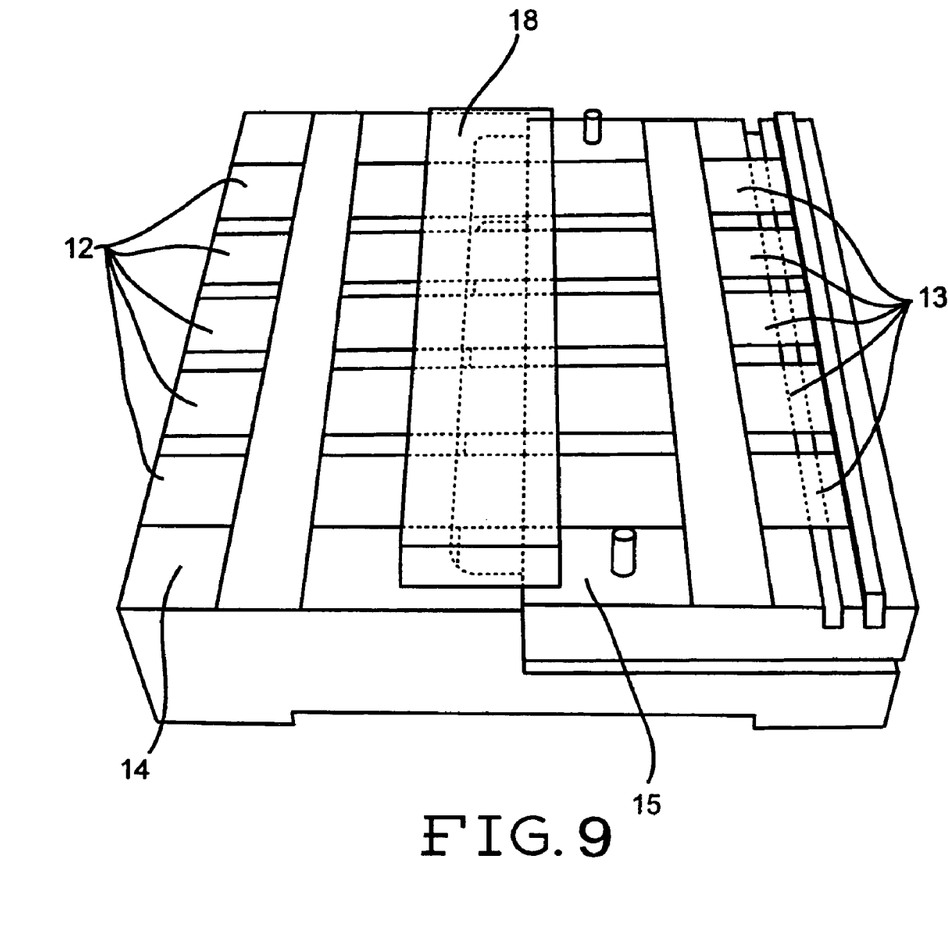
FIG. 9 illustrates a top perspective view of the first and second members of FIG. 8 with a press-member having been located over overlapping areas of the second member coupons which overlap the first member coupons.

FIG. 9 illustrates a top perspective view of the first and second members 14 and 15 of FIG. 8 with the press-member 18 having been located over the overlapping areas 49 (as shown by FIG. 7) of the second member coupons 13 which overlap the first member coupons 12. The press-member 18 may press the second member coupons 13 towards the first member coupons 12. In such manner, the adhesive 11 (as shown by FIG. 7) may be compressed between the first and second member coupons 12 and 13 in order to adhere the overlapping areas 49 (as shown by FIG. 7) of the second member coupons 13 to the first member coupons 12.

Figure 10:
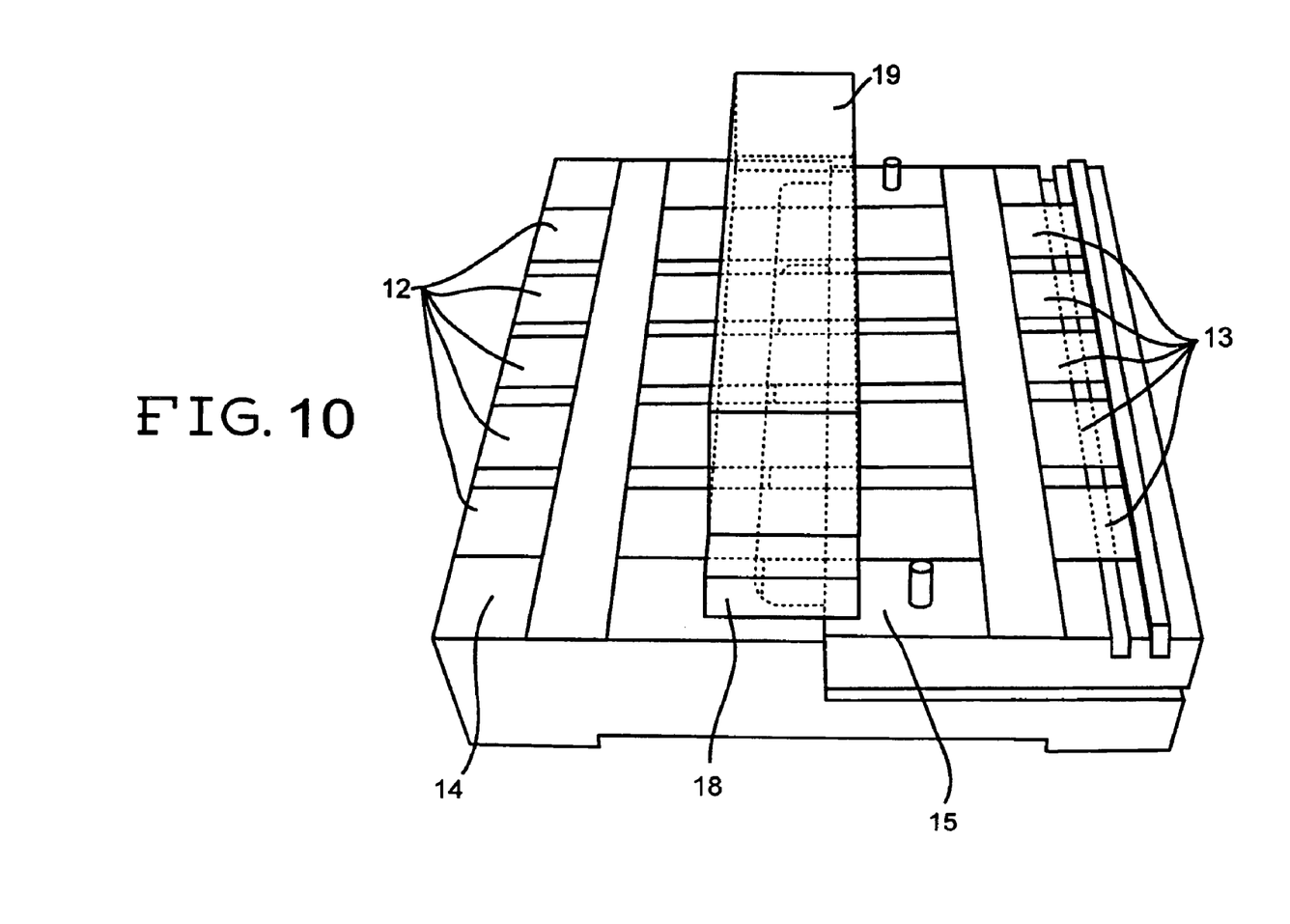
FIG. 10 illustrates a top perspective view of the first and second members of FIG. 9 with a weight having been located on the press-member.

FIG. 10 illustrates a top perspective view of the first and second members 14 and 15 of FIG. 9 with the weight 19 having been located on the press-member 18. The weight 19 may press the press-member 18 against the second member coupons 13 to further press the second member coupons 13 towards the first member coupons 12. As a result, the adhesive 11 (as shown by FIG. 7) may be further compressed between the first and second member coupons 12 and 13 in order to further adhere the first and second member coupons 12 and 13 together.

Figure 11:
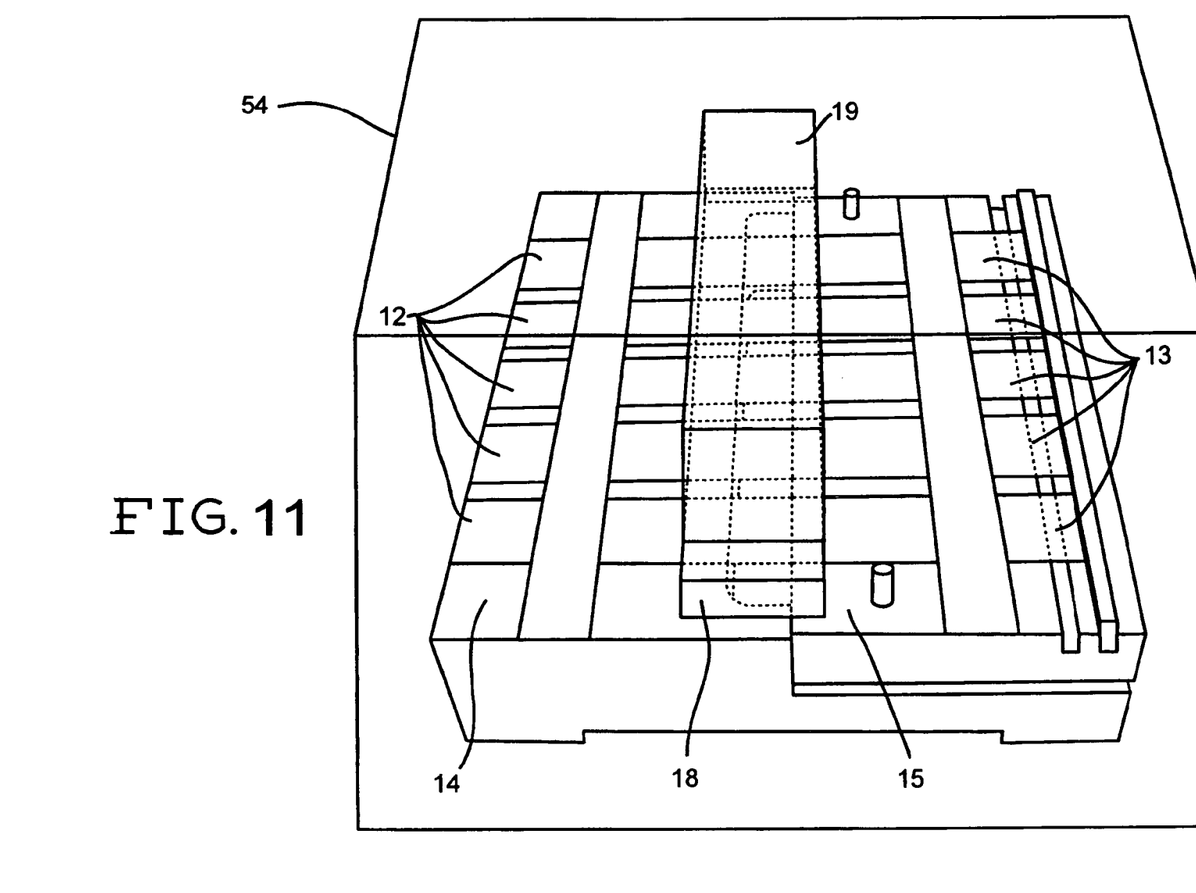
FIG. 11 illustrates a top perspective view of the first and second members of FIG. 10 with the assembled apparatus having been placed in an autoclave.

FIG. 11 illustrates a top perspective view of the first and second members 14 and 15 of FIG. 10 with the apparatus 10 having been placed in an autoclave 54. The autoclave 54 may heat the adhesive 11 (as shown by FIG. 7) to allow the adhesive 11 to cure to adhere the first and second member coupons 12 and 13 together.

Figure 12:
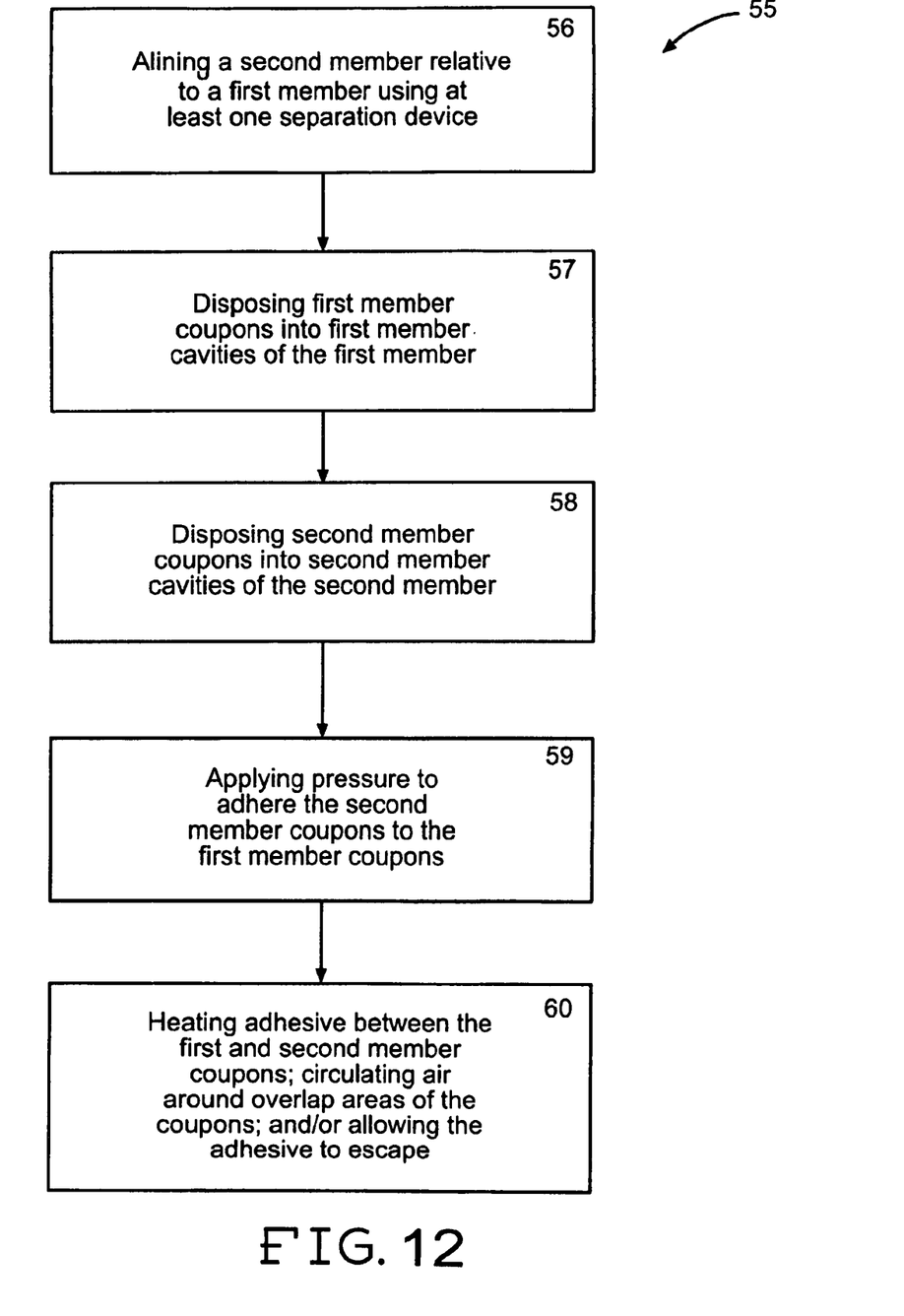
FIG. 12 illustrates a flowchart of one embodiment of a method for adhering coupons together for adhesive shear testing.

FIG. 12 illustrates a flowchart showing one embodiment of a method 55 for adhering coupons 12 and 13 together for adhesive shear testing. In step 56, a second member 15 may be aligned relative to a first member 14 using at least one separation device 16. The at least one separation device 16 may locate at least one surface 37 of the second member 15 at a distance apart from at least another surface 20 of the first member 14. The separation device 16 may comprise at least one shim. Step 56 may comprise disposing the at least one separation device 16 on the first member 14, and disposing the second member 15 on the at least one separation device 16. The second member 15 may be secured to the first member 14 by inserting at least one pin 35 into at least one hole 36.

In step 57, a plurality of first member coupons 12 may be disposed into first member cavities 22 of the first member 14. Side surfaces 25 and 26 of each first member coupon 12 may be abutted against respective spaced-apart side-walls 23 and 24 of each respective first member cavity 22. The first member coupons 12 may be abutted against at least one surface 38 of the second member 15. In step 58, a plurality of second member coupons 13 may be disposed into second member cavities 41 of the second member 15 against at least one adjustable alignment device 17.

Side surfaces 44 and 45 of each second member coupon 13 may be abutted against respective spaced-apart side-walls 42 and 43 of each respective second member cavity 41. Overlap areas 49 of the second member coupons 13 may be controllably overlapped relative to the first member coupons 12 using at least one adjustable alignment device 17. Adhesive 11 may be disposed between the overlap areas 49 of the second member coupons 13 and the first member coupons 12.

The at least one separation device 16 may control a height of the adhesive 11 between the first member coupons 12 and the second member coupons 13. The at least one adjustable alignment device 17 may control a length of the adhesive 11 in the overlap areas 49 between the first member coupons 12 and the second member coupons 13. The at least one adjustable alignment device 17 may comprise at least one of an adjustable stopper and an adjustable surface of at least one of the first and second members 14 and 15.

In step 59, pressure may be applied to adhere the second member coupons 13 to the first member coupons 12 using the adhesive 11. At least one of a weight 19 and a press-member 18 may be used to press the second member coupons 13 and the first member coupons 12 towards one another to compress the adhesive 11 between the first and second member coupons 12 and 13. In step 60, at least one of the following may occur: the adhesive 11 between the first member coupons 12 and the second member coupons 13 may be heated; air 32 may be circulated around the overlap areas 49 using at least one groove 27 and/or slot 31 disposed in at least one of the first and second members 14 and 15; and the adhesive 11 may escape from the overlap areas 49 through the at least one groove 27 and/or slot 31.

In other embodiments, one or more of the steps of the method 55 may be altered, not followed, changed in order, and/or one or more additional steps may be added.

One or more embodiments of the disclosure may resolve one or more issues experienced by one or more of the conventional apparatus and/or methods due to one or more of the following: the use of an accurate weight system to adhere the coupons; the use of a precise coupon overlap measuring system to control the overlap size of the adhesive; the ability to allow adhesive to squeeze out from the coupons during bonding; the ease of removing the adhered coupons from the fabrication apparatus; the ease of controlling bond thickness/height of the adhesive used to adhere the coupons; the use of tooling having minimal parts thereby decreasing cost; the avoidance of a cutting process to cut the post-bond coupons thereby maintaining the integrity of the coupon bond-line; and/or may resolve one or more other types of issues.

It should be understood, of course, that the foregoing relates to exemplary embodiments of the disclosure and that modifications may be made without departing from the spirit and scope of the disclosure as set forth in the following claims.

We claim:

1. An apparatus for adhering coupons together for adhesive shear testing comprising:
   a first member having at least one first member cavity for holding at least one first member coupon;
   a second member having at least one second member cavity for holding an overlapping area of at least one second member coupon adjacent to and separate from said at least one first member coupon in order to adhere the overlapping area of said at least one second member coupon to said at least one first member coupon;
   at least one alignment device comprising at least one of a stopper or a surface of at least one of said first or second members for controlling a size of the overlapping area; and
   at least one separation device for controlling a separation distance between the overlapping area of said at least one second member coupon and said at least one first member coupon.

2. The apparatus of claim 1 wherein the first member comprises a base member and the second member comprises a separate top member.

3. The apparatus of claim 1 wherein the first member comprises a plurality of adjacent first member cavities each having side-walls spaced apart to abut against respective side surfaces of a separate one of said at least one first member coupon.

4. The apparatus of claim 1 wherein the second member comprises a plurality of adjacent second member cavities each having side-walls spaced apart to abut against respective side surfaces of a separate one of said at least one second member coupon.

5. The apparatus of claim 1 wherein the overlapping area of said at least one second member coupon is adhered to said at least one first member coupon using adhesive, the at least one alignment device controlling a length of the adhesive and the at least one separation device controlling a height of the adhesive.

6. The apparatus of claim 1 wherein the at least one alignment device comprises the stopper, and the second member comprises a plurality of slots at different locations for inserting the stopper into the plurality of slots at different locations to control the size of the overlapping area based on which of the slots the stopper is inserted into.

7. The apparatus of claim 1 wherein the at least one separation device comprises a shim.

8. The apparatus of claim 7 wherein the shim is disposed on the first member and the second member is disposed on the shim, a height of the shim controlling the separation distance between the overlapping area of said at least one second member coupon and said at least one first member coupon.

9. The apparatus of claim 1 further comprising at least one pin for securing the second member to the first member.

10. The apparatus of claim 9 wherein the at least one pin is attached to the first member, and the at least one pin extends through at least one hole in the second member.

11. The apparatus of claim 1 further comprising a press-member for pressing adhesive between the overlapping area of said at least one second member coupon and said at least one first member coupon.

12. The apparatus of claim 1 wherein the first member and the second member are made of at least one of a non-stick material or a non-stick plastic.

13. The apparatus of claim 1 wherein at least one of the first member or the second member have a groove for at least one of circulating air around the overlapping area or for allowing adhesive to escape from the overlapping area.

14. The apparatus of claim 1 wherein the second member is disposed over a surface of the first member.

15. An apparatus for adhering coupons together for adhesive shear testing comprising;
   a first member having at least one first member cavity for holding at least one first member coupon;
   a second member having at least one second member cavity for holding an overlapping area of at least one second member coupon adjacent to and separate from said at least one first member coupon in order to adhere the overlapping area of said at least one second member coupon to said at least one first member coupon;
   at least one alignment device for controlling a size of the overlapping area; and
   at least one separation device comprising a shim for controlling a separation distance between the overlapping area of said at least one second member coupon and said at least one first member coupon.

16. The apparatus of claim 15 wherein the at least one alignment device comprises at least one of a stopper or a surface of at least one of said first or second members.

17. The apparatus of claim 16 wherein the at least one alignment device comprises the stopper, and the second member comprises a plurality of slots at different locations for inserting the stopper into the plurality of slots at different locations to control the size of the overlapping area based on which of the slots the stopper is inserted into.

18. The apparatus of claim 15 wherein the shim is disposed on the first member and the second member is disposed on the shim, a height of the shim controlling the separation distance between the overlapping area of said at least one second member coupon and said at least one first member coupon.

19. The apparatus of claim 15 further comprising at least one pin for securing the second member to the first member.

20. The apparatus of claim 19 wherein the at least one pin is attached to the first member, and the at least one pin extends through at least one hole in the second member.

21. An apparatus for adhering coupons together for adhesive shear testing comprising:
   a first member having at least one first member cavity for holding at least one first member coupon;
   a second member having at least one second member cavity for holding an overlapping area of at least one second member coupon adjacent to and separate from said at least one first member coupon in order to adhere the overlapping area of said at least one second member coupon to said at least one first member coupon;
   at least one pin for securing the second member to the first member:
   at least one alignment device for controlling a size of the overlapping area; and
   at least one separation device for controlling a separation distance between the overlapping area of said at least one second member coupon and said at least one first member coupon.

22. The apparatus of claim 21 wherein the at least one alignment device comprises at least one of a stopper or a surface of at least one of said first or second member.

23. The apparatus of claim 22 wherein the at least one alignment device comprises the stopper, and the second member comprises a plurality of slots at different locations for inserting the stopper into the plurality of slots at different locations to control the size of the overlapping area based on which of the slots the stopper is inserted into.

24. The apparatus of claim 21 wherein the at least one separation device comprises a shim.

25. The apparatus of claim 24 wherein the shim is disposed on the first member and the second member is disposed on the shim, a height of the shim controlling the separation distance between the overlapping area of said at least one second member coupon and said at least one first member coupon.

26. The apparatus of claim 21 wherein the at least one pin is attached to the first member, and the at least one pin extends through at least one hole in the second member.

* * * * *